United States Patent
Epstein et al.

(10) Patent No.: US 6,535,759 B1
(45) Date of Patent: Mar. 18, 2003

(54) METHOD AND DEVICE FOR LOCATING AND MAPPING NERVES

(75) Inventors: Richard Epstein, McGaw Park, IL (US); David G. Abichaker, West Roxbury, MA (US); Richard P. Rego, Mansfield, MA (US)

(73) Assignee: Blue Torch Medical Technologies, Inc., Ashland, MA (US)

( * ) Notice: Subject to any disclaimer, the term of this patent is extended or adjusted under 35 U.S.C. 154(b) by 0 days.

(21) Appl. No.: 09/692,418

(22) Filed: Oct. 20, 2000

Related U.S. Application Data

(63) Continuation-in-part of application No. 09/303,501, filed on Apr. 30, 1999, now Pat. No. 6,259,945.

(51) Int. Cl.⁷ .................................................. A61B 5/05
(52) U.S. Cl. ....................................................... 600/547
(58) Field of Search ............................... 600/547, 548, 600/554, 555; 604/116; 606/32; 607/116

(56) References Cited

U.S. PATENT DOCUMENTS

| | | |
|---|---|---|
| 3,682,162 A | 8/1972 | Colyer |
| 4,515,168 A | 5/1985 | Chester et al. |
| 5,081,990 A * | 1/1992 | Deletis .......................... 600/555 |
| 5,284,153 A | 2/1994 | Raymond et al. |
| 5,284,154 A | 2/1994 | Raymond et al. |
| 5,713,828 A | 2/1998 | Coniglione |
| 5,775,331 A | 7/1998 | Raymond et al. |
| 5,860,909 A | 1/1999 | Mick et al. |

OTHER PUBLICATIONS

Nag et al, American Brachytherapy Society (ABS) survey of Current Clinical Practice for Permanent Brachytherapy of Prostate Cancer, Apr. 1, 1998, pp. 1–17.
What is Brachytherapy, ProSeed, Inc., 1999 pp. 1–3.

* cited by examiner

*Primary Examiner*—George Manuel
(74) *Attorney, Agent, or Firm*—Sterne, Kessler, Goldstein & Fox

(57) ABSTRACT

The present application discloses a method and device for locating and mapping the cavernosal nerve bundle by electro-stimulation to enable safe and effective implantation of radioactive seeds for prostate brachytherapy. By locating and mapping the cavernosal nerve bundle prior to seed implantation, the brachytherapist can make intra-operative decisions to avoid mechanical and radiational injury to the nerve which results in impotency or other prostate-Urethral complications. The device of the invention takes the form of an automated closed-looped electro-stimulating system having a handle for manipulating the device, a stimulating tip for applying an electro-stimulus to a tissue site, a control unit to activate and terminate application of the electro-stimulus and to interpret a tumescence response, a sensor for detecting and measuring a tumescence response, a patient ground return, and a display monitor to indicate the nature, stability and strength of the tumescence response to the brachytherapist. If the control unit concludes that the applied electro-stimulus failed to evoke a tumescence response in excess of a pre-determined baseline and that the tissue lacks cavernosal nerve bundle fibers, radioactive seeds can be implanted in the prostate through the stimulating tip which also serves as a brachytherapy seed implantation needle. Alternatively, the coordinates of the tissue site can be mapped on the perineal grid or on a pre-plan grid for later seed implantation.

13 Claims, 5 Drawing Sheets

METHOD AND DEVICE FOR LOCATING AND MAPPING NERVES

CROSS-REFERENCE TO RELATED APPLICATIONS

Applicants file the instant application as a continuation-in-part of commonly assigned U.S. application Ser. No. 09/303,501 filed on Apr. 30, 1999 now U.S. Pat. No. 6,259,945 and entitled Method and Device for Locating a Nerve (the '501 application). The instant application incorporates herein the disclosure of the '501 application, in its entirety, by reference.

BACKGROUND OF THE INVENTION

1. Field of the Invention

The present invention relates to a non-invasive method and device for locating and mapping nerves and nerve bundles by electro-stimulation. More particularly, the present invention relates to a method and device for locating and mapping the cavernosal nerve bundle by electro-stimulation to assist in safe and effective implantation of radioactive seeds for prostate brachytherapy or to enhance any other non-invasive or minimally invasive form of prostate cancer therapy.

2. Related Art

Many methods of therapy are available to treat localized prostate cancer Such methods include, but are not limited to, radical prostatectomy, modifiedradical prostatectomy, external beam radiation therapy (EBRT), brachytherapy, cryotherapy, hormonal therapy, and careful observation of the gland. Successful prostate cancer therapy results in the removal or destruction of cancerous prostate tissue without injury to the nerves or tissue associated with the surrounding anatomy, particularly, the cavernosal nerve associated with penile tumescence or the urethral anatomy.

One minimally invasive method of therapy, prostate brachytherapy, involves the implantation of radioactive seeds in an area proximate to cancerous prostate tissue, but sufficiently distant from healthy prostate tissue. The radioactive seeds are implanted in the prostate by a seed delivery needle or applicator which is passed through the patient's perineum and into the prostate. Although in practice since 1913, prostate brachytherapy has recently gained popularity in light of patient dissatisfaction with radical and modified-radical prostatectomies (particularly, loss of penile tumescence (impotency) and urethral complications) and the minimally invasive nature of prostate brachytherapy.

While prostate brachytherapy qualifies as a minimally invasive method of therapy, the nerves and tissue of the surrounding anatomy are susceptible to injury since the brachytherapist cannot visualize the same. For example, if the tip of the seed delivery needle contacts or pierces the cavemosal nerve bundle, function of the nerve could be irreparably impaired, resulting perhaps in impotency. In addition, if the radioactive seeds of the brachytherapy method are positioned too close to the cavernosal nerve bundle, the seeds could destroy the cavernosal nerve fibers, again resulting in impotence or related complications. For such reasons, care should be exercised when selecting implantation sites and routes of delivery for the radioactive seeds of prostate brachytherapy.

The success of prostate brachytherapy can be improved if the brachytherapist refers to a guide or map of the diseased prostate to select safe and effective seed implantation sites and routes of delivery. With "pre-plan" brachytherapy, a measurement of the patient's prostate is taken several weeks prior to implantation of the radioactive seeds. Based on those measurements, the brachytherapist plots seed implantation coordinates on a grid or template which corresponds to the height and width of the prostate. While pre-plan guided brachytherapy facilitates implantation of radioactive seeds, it fails to provide any information on location of the cavemosal nerve bundle to avoid contact with the seed delivery needle (mechanical nerve injury) or unnecessary exposure to the radioactive material of the seeds (radiational nerve injury). In addition, pre-plan guided brachytherapy cannot account for changes in the size or shape of the prostate subsequent to the measurements taken weeks prior.

CT-guided brachytherapy, developed by the Memorial Sloan Kettering Cancer Center, relies on images generated by computed tomography to yield a computer-programmed plan of radioactive seed implantation. Although CT-guided brachytherapy provides more detailed information on the size, shape and vascular structure of the prostate gland, it cannot determine the exact location of the cavemosal nerve bundle to reduce mechanical or radiational injury.

Transrectal ultrasound brachytherapy relies on volume studies to determine the size and shape of the diseased prostate. Coordinates for the proper implantation of radioactive seeds are based on the volume study information and plotted on a pre-plan grid. To implant the radioactive seeds, the brachytherapist advances a radioactive seed delivery needle into the prostate through coordinates plotted on a grid positioned proximate the perineum. The coordinates plotted on the perineal grid correspond to the coordinates plotted on the pre-plan grid mentioned above. As the brachytherapist advances the seed delivery needle through the perineal grid and into the prostate, an image of the advancing seed delivery needle appears on the monitor of the transrectal ultrasound. When the seed delivery needle has reached the proper position interior of the prostate, the brachytherapist deposits and implants the radioactive seeds in the cancerous tissue of the prostate.

Some brachytherapists combine transrectal ultrasound with fluoroscopy to provide a three-dimensional transperineal image of the prostate. While either method provides a real time three-dimensional image of the prostate and its vascular structure, it too lacks the ability to effectively locate and map the cavernosal nerve bundle to avoid unintended contact with a seed delivery needle or radioactive seed which could result in mechanical or radiational damage.

Since brachytherapists (and clinicians practicing others forms of non-invasive or minimally invasive prostate cancer therapy) operate "blindly" with respect to the cavernosal nerve bundle (i.e., no surgical exposure or open visualization of the nerve bundle), a need exists for a device which locates and maps the cavernosal nerve bundle prior to application of brachytherapy to avoid mechanical or radiational injury to the nerve.

Devices for locating a nerve for delivery of anesthesia by needle or syringe are disclosed in U.S. Pat. No. 4,515,168 to Chester et al. and U.S. Pat. No. 3,682,162 to Colyer. While the mentioned patents use electro-stimulation to indicate needle position relative to the nerve, such devices rely heavily on the skill of the clinician and fail to account for the complex and delayed response patterns of autonomic nerves, such as the cavernosal nerve. See, e.g., p. 2 of the '501 application incorporated herein by reference.

In U.S. Pat. Nos. 5,284,153 and 5,284,154, Raymond et al. disclose a device and method to locate and protect a nerve from intra-operative injury. More particularly, the device has been configured to identify, locate and protect the cavernosal nerve while excising cancerous prostate tissue (i.e., radical or modified-radical prostatectomy). The device comprises an instrument for applying a stimulus to tissue in the area of the cavernosal nerve, a tumescence response detector, means for evaluating the detected response, means for modifying the stimulus intensity, and means for indicating the proximity of the instrument to the cavernosal nerve. Successful location of the nerve, however, appears to depend on the clinician's ability to effectively advance the stimulating instrument through the body tissue to locate the nerve. In addition, the tip of the stimulating instrument (i.e., the probe) appears more suitable for invasive therapies, such as radical or modified-radical prostatectomy, rather than a minimally invasive therapy, such as brachytherapy.

In an attempt to reduce reliance on the skill of the clinician, Raymond et al. developed a closed-loop system for locating the cavernosal nerve for radical prostatectomy. The apparatus of U.S. Pat. No. 5,775,331 (the '331 patent) comprises a stimulating probe having an array of electrodes, an automatic control means, and a tumescence response detector. Using the electrode array of the stimulating probe, a clinician applies a stimulus to an area of tissue believed to contain the cavernosal nerve. The response detecting means records a tumescence response, if any, and the control means automatically modifies activation of the electrode array (i.e., subsequent sites of stimulation) based on an evaluation of the response to prior stimulation. The steps are repeated until the nerve has been located.

Like the prior device to Raymond et al., the apparatus of the '331 patent comprises a probe structure better suited for invasive prostate cancer therapy methods, such as radical prostatectomy.

Subsequent to development of the device disclosed in the '331 patent, Raymond et al. realized that other factors associated with the patient or the clinical environment (e.g., the patient's blood pressure, inadvertent manipulation of the response detector, or the amount of anesthesia administered to the patient) could evoke a change in tumescence. See pp. 3–4 of the '501 application. The method and device of the '501 application seeks to avoid a misinterpretation of tumescence by assessing the "stability" or "unstability" of the response signal prior to an attempt to locate the nerve by electro-stimulation. To assess the stability of the tumescence signal, the device of the '501 application compares the tumescence signal (prior to application of electro-stimulation) to a library of stored reference values which correspond to a state of stability or unstability. If the tumescence signal has been characterized as unstable, the device waits for the tumescence signal to stabilize (or for an over-ride command) before proceeding with electro-stimulation.

The device of the '501 application effectively addresses the complex factors associated with stimulation of the cavernosal nerve to avoid the misinterpretation of tumescence response signals which results in inaccurate or delayed locating of the cavernosal nerve.

In light of the many considerations discussed above, the need exists for a device which accurately locates and maps the cavernosal nerve bundle to facilitate application of invasive, minimally invasive, and non-invasive methods of therapy for prostate cancer.

Another need exists for a device which assesses the stability of the tumescence signal prior to any attempt to locate the cavernosal nerve by electro-stimulation to avoid misinterpretation of any change in the tumescence signal evoked by unrelated factors associated with the patient or clinical field, rather than by electro-stimulation.

A further need exists for a device for mapping and locating the cavernosal nerve bundle to reduce or avoid injury associated with minimally invasive or non-invasive (blind) methods of prostate cancer therapy (e.g., mechanical nerve injury resulting from direct contact with seed implantation needles or radiational nerve injury resulting from exposure to radioactive seeds implanted in the prostate and intended to destroy only cancerous prostate tissue).

Yet another need exists for a device which locates and maps the cavernosal nerve bundle and which mates with conventional equipment for applying known methods of prostate cancer therapy (e.g., radioactive seed implantation needles, cryotherapy needles, or pre-loaded seed cartridges).

Still another need exists for a device which can store information on the size and shape of the prostate, past therapy application sites, and the location of the cavernosal nerve bundle for future therapy applications.

SUMMARY OF THE INVENTION

It was with the preceding needs in mind that the present invention was developed. The present invention represents a modification and improvement to the Method and Device for Locating a Nerve disclosed and claimed in the '501 application. It comprises a method and device for locating and mapping the cavernosal nerve bundle by electro-stimulation to enable safe and effective implantation of radioactive seeds for prostate brachytherapy. By locating and mapping the cavernosal nerve bundle prior to seed implantation, the brachytherapist can make intra-operative decisions to avoid mechanical and radiational injury to the nerve which results in impotency or other prostate-Urethral complications. The device of the invention takes the form of an automated closed-looped electro-stimulating system having a handle for manipulating the device, a stimulating tip for applying an electro-stimulus to a tissue site, a control unit to activate and terminate application of the electro-stimulus and to interpret a tumescence response, a sensor for detecting and measuring a tumescence response, a patient ground return, and a display monitor to indicate the nature, stability and strength of the tumescence response to the brachytherapist. If the control unit concludes that the applied electro-stimulus failed to evoke a tumescence response in excess of a pre-determined baseline and that the tissue lacks cavernosal nerve bundle fibers, radioactive seeds can be implanted in the prostate through the stimulating tip which also serves as a brachytherapy seed implantation needle.

In another embodiment of the invention, a kit for locating and mapping a nerve to avoid injuring the nerve during application of therapy has been provided. The kit comprises a device for locating the nerve using electro-stimulation and a grid for mapping coordinates corresponding to tissue sites. The device for comprises means for detecting and measuring a response signal and a change in the response signal evoked by application of an electro-stimulus to the nerve, means for analyzing the response signal provided by said detecting and measuring means to determine its stability, means for applying an electro-stimulus to an area of tissue, and means for interpreting a change in the signal evoked by application of the electro-stimulus to the nerve to the determine the location of the nerve. The means for applying the electro-stimulus to the tissue comprises a removable array of electrodes to determine the location of the nerve in an effort to avoid the nerve during the excision of tissue associated with radical prostatectomy. In another embodiment, the means for applying an electro-stimulus to the tissue comprises a removable needle for applying an electro-stimulus to the tissue area and for administering minimally invasive prostate cancer therapy through the perineum of the patient. The needle comprises a brachytherapy seed implantation needle. In another embodiment, the needle comprises a cryosurgery needle. The response detecting and measuring means comprises distensible fluid filled tubing.

A method for locating and mapping cavemosal nerve fibers to avoid injuring the nerve fibers during application of prostate cancer therapies has been provided, as well. The method comprises the steps of detecting and measuring a tumescence response signal from the cavemosal nerve, determining the stability of the tumescence response signal and characterizing it as stable or unstable, applying an electro-stimulus to a tissue site believed to contain the cavernosal nerve fibers if the tumescence response signal has been characterized as stable, detecting and measuring any change in the tumescence response signal evoked by application of the electro-stimulus, interpreting any change in the tumescence response signal evoked by application of the electro-stimulus, and determining if the tissue site contains cavernosal nerve fibers. The method further comprises the step of applying prostate cancer therapy to the tissue site it has been determined that the tissue site lacks cavemosal nerve fibers.

BRIEF DESCRIPTION OF THE FIGURES

Various objects, features and attendant advantages of the device and method of the present invention can be more fully appreciated and understood from the following detailed description of the preferred embodiments, when considered in connection with the accompanying figures, in which.

DETAILED DESCRIPTION OF THE PREFERRED EMBODIMENTS

As discussed above, the present invention represents a modification and an improvement to the Method and Device for Locating a Nerve disclosed and claimed in the '501 application. Prior to discussing the method of the present invention, the structure of the device shall be described with particular reference to the accompanying figures and to the disclosure of the '501 application. Although Applicants make reference to specific sections of the prior application, the disclosure of the '501 application is incorporated herein, in its entirety, by reference.

Figure 1:
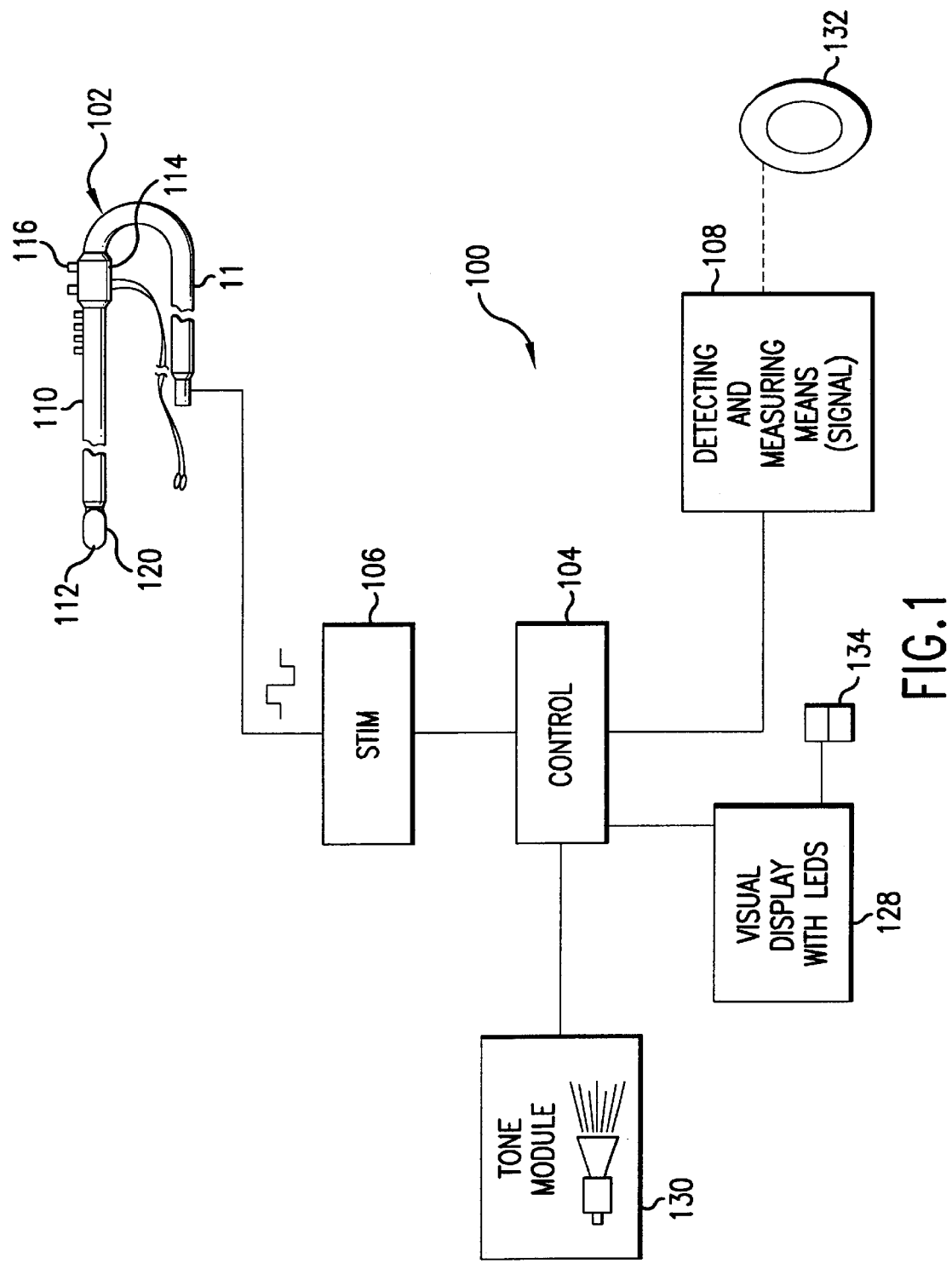
FIG. 1 represents a schematic of the device of the present invention. It corresponds in structure to FIG. 1 of the '501 application.

FIG. 1 of the accompanying drawings illustrates a schematic of the major components of the device of the present invention, as previously disclosed in FIG. 1 of the '501 application. Device 100 comprises stimulus applying means 102, control means 104, stimulating circuit 106, and tumescence response or signal detection means 108. To locate the cavernosal nerve, tumescence response or signal detection means 108 preferably takes the form of a tumescence monitor 132 comprising distensible tubing filled with a conductive fluid. However, device 100 could comprise other means for detecting a response signal disclosed in the '501 application.

As used with invasive prostate cancer therapy (e.g., radical prostatectomy), stimulus applying means 102 takes the form of a probe 110 having a stimulating tip 112, a handle 114, a switch panel 116, and a cable 118 for connecting probe 110 to control means 104 at 122. An array of electrodes 120 positioned about stimulating tip 112 deliver a pulse of current (an electro-stimulus) to the area of tissue believed to contain the nerve to be located.

FIG. 1 further discloses a visual display 128 with light emitting diodes (LEDS) and an audible tone module 130 for visually displaying and audibly communicating data to the user (such as the intensity of the electro-stimulus or information concerning the stability of a tumescence signal). An up/down switch 134 enables manual adjustment of the stimulating current, if desired.

A complete description of the structure illustrated in accompanying FIG. 1 appears in the '501 application on pp. 7–9 and Applicants incorporate the disclosure herein by reference.

As discussed above in the Background of the Invention section, device 100 for locating a nerve, as disclosed in the '501 application and in accompanying FIG. 1, can be distinguished from prior nerve locators in that it comprises computer software for determining if the tumescence response signal (or a change in the tumescence response signal) can be characterized as stable (i.e., tumescence response signal or change in tumescence response signal not attributable to external factors associated with the patient or the clinical field) prior to applying electro-stimulation to a tissue site to prevent misinterpretation of the tumescence response and to enhance the locating accuracy of the device. The signal stability method and other methods of operation for locating a nerve with device 100 (particularly, the cavernosal nerve for radical prostatectomy) have been described on pp. 9–20 of the '501 application and Applicants incorporate the same disclosure herein by reference.

Figure 2:
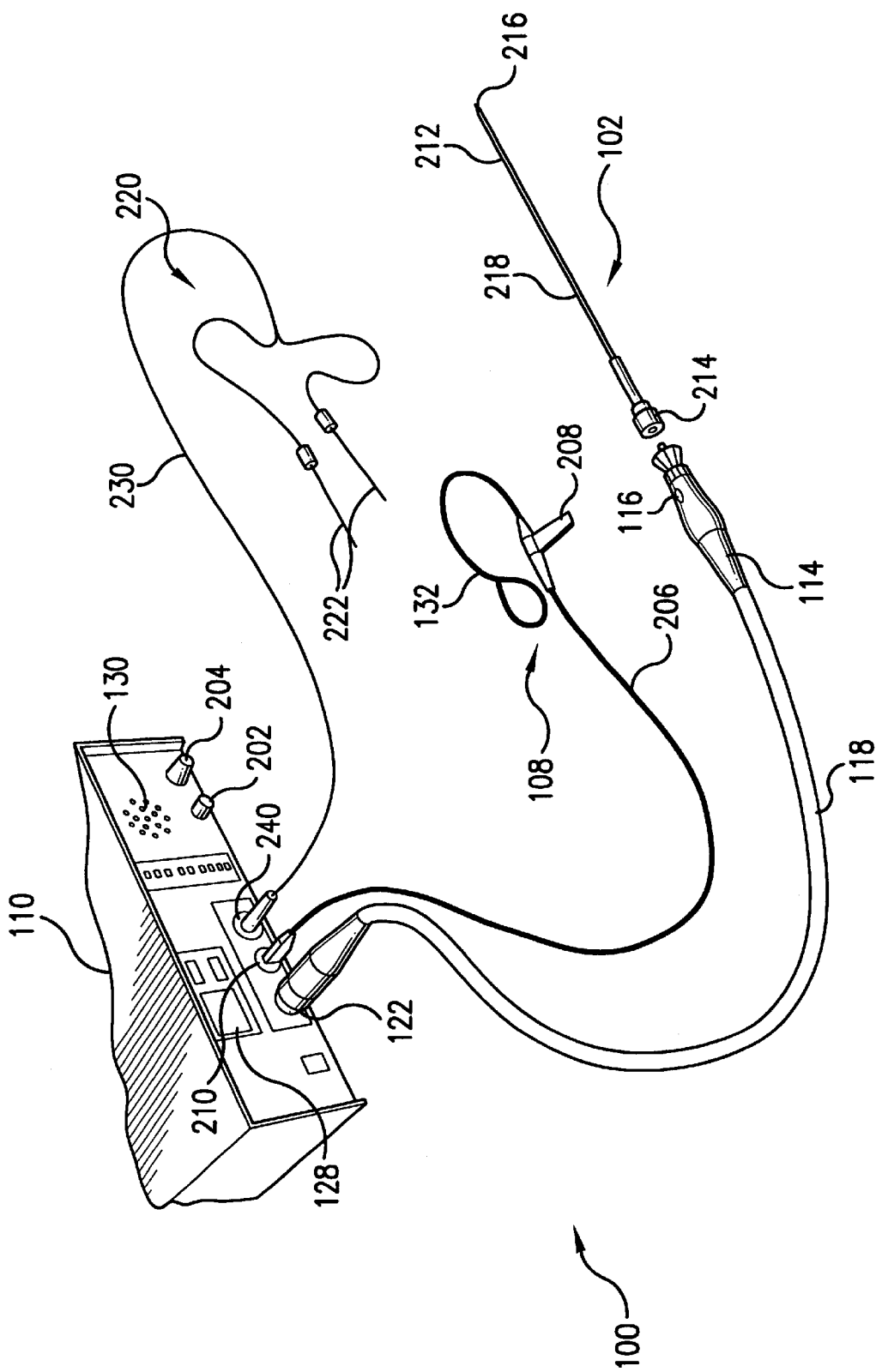
FIG. 2 illustrates the components of the device.

FIG. 2 illustrates an embodiment of control unit 100 shown schematically in FIG. 1. FIG. 2 further discloses visual display 128 and audible tone module 130 having control dials 202 and 204 for selecting either a variable pitched tone (202) or a pulsed tone (204). Tumescence response or signal monitor 132, having a lead 206 and a clip 208 for securing the lead to the patient's clinical dress, makes an electrical connection with control unit 110 at input 210.

In accordance with the objectives of the present invention, stimulus applying means 102 of FIG. 2 has been modified to facilitate safe and effective application of prostate brachytherapy. For that embodiment of the present invention, stimulus applying means 102 takes the form of a brachytherapy seed implantation needle 212 which has been modified to mate with handle 114 at hub 214 to deliver electro-stimulation directed by control unit 110 to a tissue site. More particularly, a conventional MICK applicator (e.g., the MICK 175-TP applicator or the MICK 200-TP applicator, available from Mick Radio Nuclear Instruments, Bronx, N.Y.) or the Radioactive Seed Applicator of U.S. Pat. No. 5,860,909 to Mick et al. (the entire disclosure of which incorporated herein by reference) could be modified for use with the present invention. Brachytherapy seed implantation needle 212 has been configured to not only implant radioactive seeds in the prostate at spaced locations, but to apply electro-stimulation to diseased prostate tissue. Seed implantation needle 212 should comprise at least a body inserted needle, a removable magazine pre-loaded with radioactive seeds, a plunger or stylus for forcing the seeds into the prostate, and a series of markings 218 to indicate the depth of seed implantation.

It should be noted that only the distal-most tip 216 of seed implantation needle 212 is exposed to ensure that the needle applies an electro-stimulating pulse of appropriate charge density to a distinct tissue point or site, rather than to a broader tissue area. The remainder of seed implantation needle 212 is properly insulated using a thin dielectric material. Although the stimulus applying means of the device for brachytherapy has been described as a brachytherapy seed implantation needle, other embodiments have been envisioned and are discussed in more detail later in the disclosure.

Finally, FIG. 2 discloses a patient ground return 220 for device 100 having two needles 222 which are inserted into the patient's muscle tissue. Patient ground return 220 connects to control unit 110 by lead 230 at 240.

Figure 3:
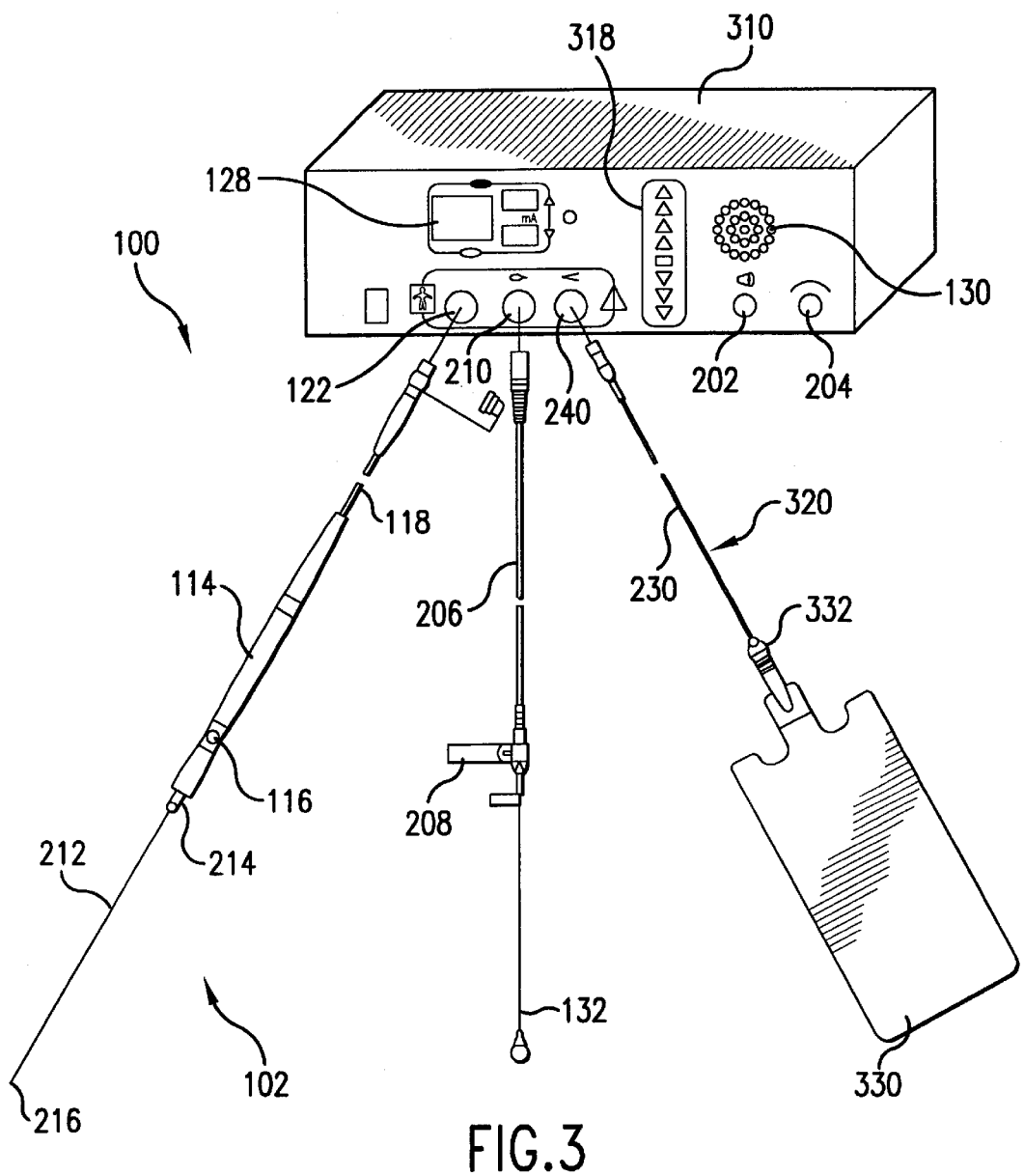
FIG. 3 illustrates other embodiments of the components of the device.

FIG. 3 illustrates another embodiment of the device for locating and mapping nerves for brachytherapy. It illustrates a second embodiment of a patient ground return 320 comprising a disposable patch electrode 330 connected to lead 230 by an alligator clip 332. Although two embodiments of a patient ground return have been disclosed (220,320), any other type of grounding device could be used so long as an adequate path for the return signal has been provided.

Figure 4:
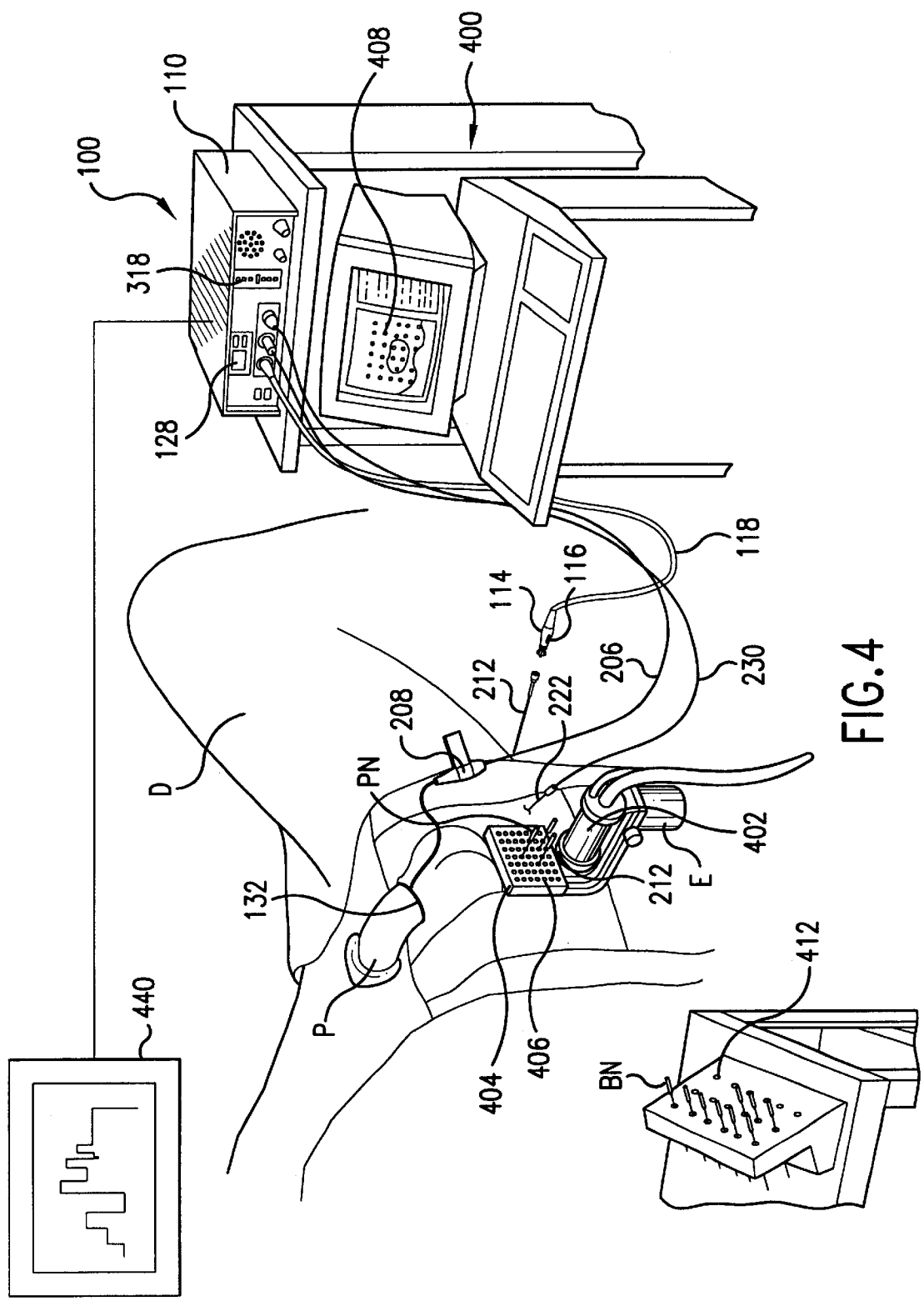
FIG. 4 illustrates use of the device of the present invention with pre-planned, transrectal ultrasound guided prostate brachytherapy.

Having described the structure of the modified device, the discussion now turns to preparation and use of device 100 for brachytherapy, a minimally invasive form of prostate cancer therapy. FIG. 4 illustrates use of device 100 for application of brachytherapy, as combined with the pre-plan and transrectal ultrasound guides discussed in the Background of the Invention section.

Device 100 appears on the right side of the figure on a shelf positioned above the monitor and hardware of an ultrasound machine 400. Stimulus applying means 102, tumescence response signal detection means 108, and patient ground return 220 are shown connected to control unit 110 by the appropriate leads. Needles 222 have been inserted into the patient's muscle tissue (specifically, the buttocks) and tumescence signal monitor 132 has been applied to the patient's penis P and positioned at the base of the shaft. In addition, lead 206 of the tumescence signal monitor 132 has been secured to surgical draping D by clamp 208 to keep lead 206 clear of the clinical environment.

A transrectal probe 402 connected to ultrasound machine 400 is shown inserted within the rectum of the patient and resting on a table extension E. A perineal grid 404 is positioned proximate to the perineum of the patient immediately above the transrectal probe. Perineal grid 404 comprises a plurality of bores 406 arranged vertically and horizontally. Bores 406 are sized to receive brachytherapy seed implantation needle 112 (or other structure capable of delivering seeds to the prostate), as well as stimulus applying means 102 of device 100. Bores 406 are provided to map coordinates or sites for implanting radioactive seeds in the cancerous tissue of the prostate. By lettering the horizontal rows of bores, and numbering the vertical rows of bores, those coordinates which correspond to appropriate seed implantation sites in the prostate can be assigned designations, such as A4, C5, and D6.

A plurality of brachytherapy seed implantation needles PN are shown positioned within bores 406 of perineal grid 404. Needles PN have been placed in those bores which correspond in position to sites within the prostate suitable for implantation of radioactive seeds (i.e., not near the cavernosal nerve or other tissue to be avoided). The needles are inserted within the bores to distances appropriate for the depth of seed implantation. That depth can be measured or determined by referring to spaced distance markings appearing on the exterior of the needle shaft (FIG. 2 at 218). A virtual grid 408, identical in bore arrangement to perineal grid 404, appears on the monitor screen of ultrasound machine 400 for visualization by the brachytherapist. The purpose of grid 408 shall be explained in more detail below, as it relates to a discussion of the transrectal ultrasound guide.

Another grid 410 appears on the left side of FIG. 4 positioned on a table and within the vision and reach of the brachytherapist. Grid 410 results from the pre-plan guide discussed above in the Background of the Invention Section. Like grid 404, grid 410 comprises a plurality of bores 412 arranged both horizontally and vertically. Bores 412 are sized to receive brachytherapy seed implantation needles BN or cartridges pre-loaded with radioactive seeds to be implanted in the prostate at specific sites and depths. Ideally, the coordinates of brachytherapy seed implantation needles BN correspond to the coordinates mapped on grid 404. Alternatively, grid 410 could be used to simply store the radioactive seed needles in a position ready for implantation by the brachytherapist.

With continuing reference to FIG. 4, after inserting the transrectal probe and receiving the pre-plan guide and grid 412 discussed above, device 100 and ultrasound machine 400 are activated. The brachytherapist begins by inserting brachytherapy seed implantation needle 212 of stimulus applying means 102 in one of bores 406 which corresponds to a position in the prostate believed to be suitable for implantation of radioactive seeds, as based on information from the pre-plan and the appearance of the prostate on the monitor of ultrasound machine 400. If it appears from the ultrasound screen that the cavernosal nerve bundle resides in the potential site of implantation, the brachytherapist maintains the position of the stimulus applying means 102 and activates course mode stimulation of device 100 by pressing the course mode button on switch panel 116. Control unit 110 runs the signal stability and course mode stimulation programs of the device (described on pp. 9–15 of the '501 application and incorporated herein by reference) to determine if the potential site of implantation contains cavemosal nerve bundle fibers. If device 100 determines that the site contains such fibers (as assessed from the tumescence response signal), device 100 is de-activated and the seed implantation needle 212 is withdrawn from grid 404 to signify that the tested tissue site (as identified by coordinate letter and number) is not appropriate for implantation in light of existing cavemosal nerve bundle fibers. If device 100 determines that the intended site of implantation does not contain cavernosal nerve bundle fibers, device 100 is de-activated, seed implantation needle is disengaged from handle 114, if necessary, and the radioactive seeds within the seed implantation needle 212 are advanced through the lumen of the needle and into the prostate by the stylus of the needle or other structure. The process is repeated until the recommended dosage of radioactive seeds have implanted in cancerous, but non-innervated areas of the prostate.

With the locating and mapping device of the invention, as supplemented by the pre-plan and transrectal ultrasound guides, brachytherapy can be applied to a diseased prostate without risk of mechanical or radiation injury to the cavernosal nerve bundle.

Figure 5:
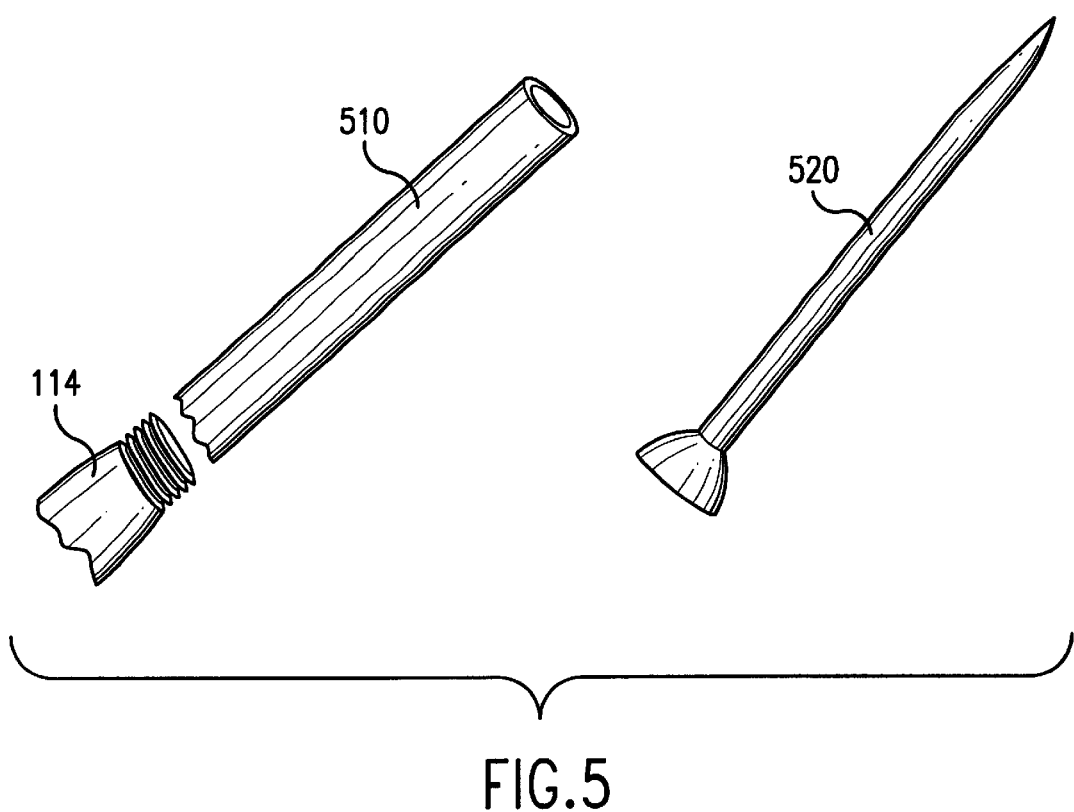
FIG. 5 illustrates two alternative embodiments of the stimulus applying means of the device.

Although the stimulus applying means 102 of device 100 has been described as a brachytherapy seed implantation needle, other instruments could be used to deliver a stimulus to a tissue site and/or implant radioactive seeds in the prostate. With reference to FIG. 5, such instruments could include, but are not limited to, a hollow threaded cannula 510 attachable to handle 114, a stylus 520 with a pencil point tip also attachable to handle 114, or electrode array 112 shown in FIG. 1 of the drawings. Both cannula 510 and stylus 520 must be properly insulated to a point just short of the tip in order to effectively apply a stimulus to a tissue site to determine the presence of cavernosal nerve bundle fibers. Using cannula 510, radioactive seeds can be delivered and implanted in the prostate using a pre-loaded cartridge or other any other needle positionable within the hollow lumen of the cannula. The radioactive seeds can be pre-loaded into the needle to be pushed through the cannula or loaded intra-operatively.

As noted above, electrode array 112 can also be used for minimally invasive prostate cancer therapies, such as brachytherapy. In that embodiment, however, only a single electrode (or all of the electrodes) of the array must be activated to effectively locate and map the cavernosal nerve bundle fibers to determine the proper location for radioactive seed implantation. In that embodiment, however, the array cannot double as a radioactive seed delivery device. Any one of the other needles or instruments discussed above could be used to deliver and implant radioactive seeds in the prostate, after the array has been removed from the handle of the device.

Finally, it is envisioned that a separate monitor for visualizing the change in tumescence in real-time could be provided to device 100. Tumescence visualizing monitor 440 appears in FIG. 4 connected control to unit 110 to display information regarding patient tumescence to make intra-operative decisions concerning the application of any type of prostate cancer therapy envisioned for the device.

With the device of the present invention, the cavernosal nerve bundle can be effectively located and mapped to avoid injury to innervated tissue or nerve fibers intra-operatively. Because the device can be modified to mate with a variety of stimulating tips (e.g., a brachytherapy seed implantation needle, a cryotherapy needle, an array of electrodes positioned on a probe, a cannula configured to receive needles containing pre-loaded radioactive seeds), it can be used to apply all types of prostate cancer therapies including invasive therapies (such as radical prostatectomy) and minimally or noninvasive "blind" therapies (such as brachytherapy or cryotherapy).

In addition, the device effectively determines the stability of a stimulation response signal to avoid misinterpretation of the signal which could result in inaccurate or delayed nerve location.

Furthermore, all information derived by the device during the application of any prostate cancer therapy (e.g., nerve location, tissue anomalies, and depth, spacing and dosage of radioactive seed implantation) can be stored in the device's memory and recalled when needed for future therapy applications.

Finally, it should be realized that while the disclosure relates to the cavernosal nerve bundle and prostate cancer, the device and its components could be modified to locate any nerve (having a detectable response) for therapeutic purposes.

While the invention has been shown and described with reference to a preferred embodiment, it should be understood by those skilled in the art that modifications to the device and method of the invention can be made without departing from the scope and spirit of the invention.

The invention is defined by the following claims.

What is claimed is:

1. A device for locating the cavernosal nerve bundle to avoid injury during application of minimally invasive and non-invasive prostate cancer therapies, comprising:
    means for detecting and measuring a tumescence response signal and a change in the tumescence response signal evoked by application of an electro-stimulus to the cavernosal nerve;
    means for analyzing the tumescence response signal provided by said detecting and measuring means to determine its stability;
    means for applying an electro-stimulus to an area of tissue; and
    means for interpreting a change in the signal evoked by application of the electro-stimulus to the cavernosal nerve to determine the location of the nerve;
    wherein said stimulus applying means is a brachytherapy needle comprising means for delivering a therapeutic agent to tissue.

2. The device of claim 1, wherein said stimulus applying means comprises a removable cannula with a hollow lumen sized to receive a pre-loaded needle containing radioactive seeds.

3. The device of claim 1, wherein said means for detecting and measuring a tumescence response signal comprises fluid-filled distensible tubing.

4. A kit for locating and mapping a nerve to avoid injuring the nerve during application of therapy, the kit comprising:
    a device for locating a nerve using electro-stimulation, said device comprising:
        means for detecting and measuring a response signal and a change in the response signal evoked by application of an electro-stimulus to the nerve;
        means for analyzing the response signal provided by said detecting and measuring means to determine its stability;
        means for applying an electro-stimulus to an area of tissue; and
        means for interpreting a change in the signal evoked by application of the electro-stimulus to the nerve to determine the location of the nerve; and
    a grid for mapping coordinates corresponding to tissue sites;
    wherein said nerve is the cavernosal nerve and said response signal corresponds to penile tumescence.

5. The kit of claim 4, wherein said means for applying an electro-stimulus to an area of tissue comprises a removable array of electrodes to determine the location of the nerve to avoid injuring the nerve during radical prostatectomy.

6. The kit of claim 4, wherein said means for applying an electro-stimulus to an area of tissue comprises a removable needle for applying an electro-stimulus to the tissue area and for administering minimally invasive prostate cancer therapy through the perineum of a human patient.

7. The kit of claim 6, wherein said needle comprises a brachytherapy seed implantation needle for applying brachytherapy to the prostate.

8. The kit of claim 6, wherein said needle comprises a cryosurgical needle for applying cryosurgery to the prostate.

9. The kit of claim 6, wherein said needle comprises a hollow lumen sized to receive a magazine of radioactive brachytherapy seeds.

10. The kit of claim 4, wherein said response detecting and measuring means comprises distensible fluid-filled tubing.

11. The kit of claim 6, wherein said grid comprises a plurality of bores which define coordinates on said grid and said grid comprises structure for positioning said grid proximate the perineum.

12. The kit of claim 11, wherein said bores of said grid correspond to tissue coordinates of the prostate.

13. A method for locating and mapping cavernosal nerve fibers to avoid injuring the nerve fibers during application of prostate cancer therapy, comprising the steps of:

a) detecting and measuring a tumescence response signal from the cavernosal nerve;

b) determining the stability of the tumescence response signal and characterizing it as stable or unstable;

c) applying an electro-stimulus to a tissue site believed to contain the cavernosal nerve fibers if the tumescence response signal has been characterized as stable;

d) detecting and measuring any change in the tumescence response signal evoked by application of the electro-stimulus;

e) interpreting any change in the tumescence response signal evoked by application of the electro-stimulus;

f) determining if the tissue site contains cavernosal nerve fibers; and g) applying prostate cancer therapy to the tissue site if it has been determined that the tissue site does not contain cavernosal nerve fibers.

* * * * *